(12) United States Patent
Qian et al.

(10) Patent No.: US 10,176,892 B2
(45) Date of Patent: Jan. 8, 2019

(54) METHOD AND SYSTEM FOR PRESENTING SUMMARIZED INFORMATION OF MEDICAL REPORTS

(71) Applicant: KONINKLIJKE PHILIPS N.V., Eindhoven (NL)

(72) Inventors: Yuechen Qian, Briarcliff Manor, NY (US); Merlijn Sevenster, Chicago, IL (US)

(73) Assignee: Koninklijke Philips N.V., Eindhoven (NL)

( * ) Notice: Subject to any disclaimer, the term of this patent is extended or adjusted under 35 U.S.C. 154(b) by 1089 days.

(21) Appl. No.: 14/014,961

(22) Filed: Aug. 30, 2013

(65) Prior Publication Data

US 2014/0172456 A1 Jun. 19, 2014

Related U.S. Application Data

(60) Provisional application No. 61/696,538, filed on Sep. 4, 2012.

(51) Int. Cl.
  *G06F 17/27* (2006.01)
  *G06F 17/30* (2006.01)
  *G16H 15/00* (2018.01)

(52) U.S. Cl.
  CPC ............ *G16H 15/00* (2018.01); *G06F 17/27* (2013.01); *G06F 17/30684* (2013.01); *G06F 17/30719* (2013.01)

(58) Field of Classification Search
  CPC .. G06F 19/322; G06F 17/27; G06F 17/30719; G06F 17/30684; G06Q 50/22; G16H 15/00

USPC ........................................................ 705/2–3
See application file for complete search history.

(56) References Cited

U.S. PATENT DOCUMENTS

| | | | |
|---|---|---|---|
| 5,664,109 A * | 9/1997 | Johnson | G06Q 40/08 705/2 |
| 2007/0260580 A1* | 11/2007 | Omoigui | G06F 17/30528 |
| 2012/0060216 A1* | 3/2012 | Chaudhri | G06Q 50/22 726/21 |
| 2013/0021346 A1* | 1/2013 | Terman | G09B 5/08 345/467 |
| 2013/0060793 A1* | 3/2013 | Bandyopadhyay | G16H 10/60 707/755 |

OTHER PUBLICATIONS

Feblowitz et al., Summarization of Clinical Information: A Conceptual Model, Mar. 31, 2011, Journal of Biomedical Informatics, vol. 44, Issue 1, pp. 688-699 (Year: 2011).*

* cited by examiner

*Primary Examiner* — Joy Chng

(57) ABSTRACT

A system and method for presenting summarized information of medical reports. The system and method receiving a plurality of medical reports, each medical report including a plurality of sections, each of the sections including text content, correlating corresponding sections of each of the medical reports into section types, extracting the text content of the sections of the medical reports for a selected section type and aggregating, into a single display, the text content of the sections of all the medical reports for the selected section type.

17 Claims, 11 Drawing Sheets

METHOD AND SYSTEM FOR PRESENTING SUMMARIZED INFORMATION OF MEDICAL REPORTS

Using current techniques, it can be cumbersome and time-consuming for radiologists to find relevant clinical information in prior radiology studies, electronic medical records ("EMRs"), pathology reports, lab reports, etc. To understand the history of the patient the radiologist typically needs to read multiple prior studies of the patient, and often information in the reports is redundant. As a result, significant wasted effort is required on the part of the radiologist.

Figure 1A:
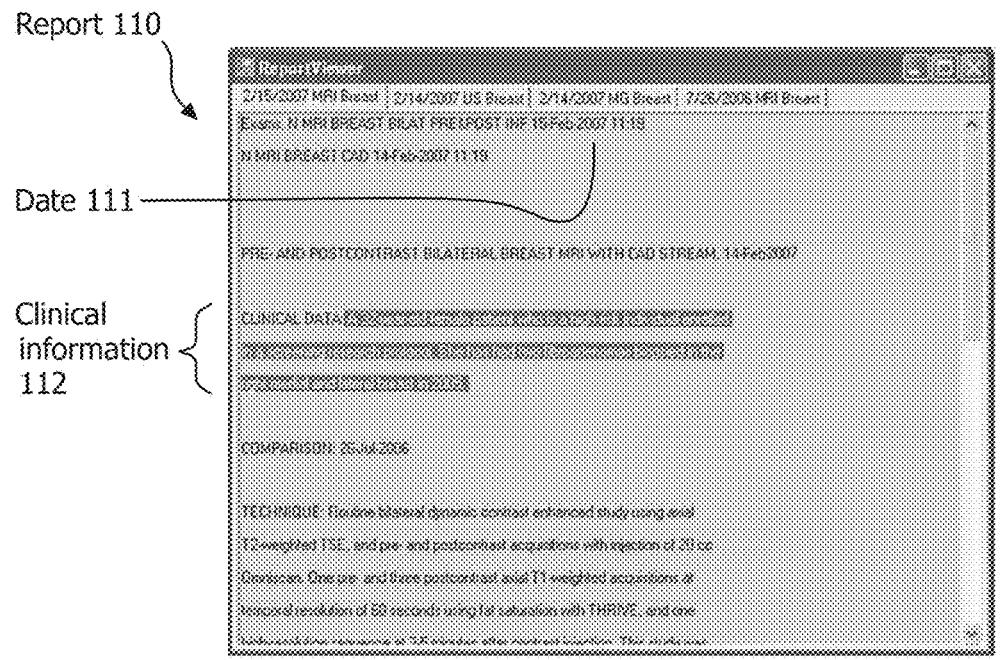
FIG. 1A shows an exemplary portion of a report of a first radiology study of a patient.

The exemplary embodiments may be further understood with reference to the following description of exemplary embodiments and the related appended drawings, wherein like elements are provided with the same reference numerals. Specifically, the exemplary embodiments relate to methods and systems for aggregating and presenting summarized patient information to radiologists. While the exemplary embodiments are described with reference to radiology reports and/or studies, those skilled in the art will understand that the principles described herein with respect to the exemplary embodiments may be applied to other medical reports and/or studies.

In evaluating patient information, radiologists need to interpret patient images in proper context. This context may include information from prior image studies, pathology studies, and laboratory exams. Generally, a radiologist opens and reads prior studies one by one, examining images and reports sequentially, until there is sufficient information to start evaluating and interpreting a current study. Typically, a radiologist will look for primary findings, accidental findings, and follow-up recommendations from prior studies. Using existing procedures, it can be cumbersome and time-consuming for a radiologist to find relevant clinical information in prior radiology studies, EMRs, pathology reports, lab reports, etc., because of the need to open and read each prior report one by one. Thus, the radiologist's time is not used as efficiently as possible. The exemplary embodiments present methods and systems for aggregating and presenting summarized patient information to radiologists, in order that their time may be used optimally.

As described above, to obtain contextual clinical information for a patient, a radiologist must open studies and read reports. A report of a radiology study consists of multiple sections of information; in this description of a report of a radiology study, the term "current study" refers to the study being described in the report, not the study to be performed by a radiologist based on the review of the report. The Clinical Information section (also known as "Clinical Data" or "Clinical History") typically describes signs and symptoms, the reason for an exam, patient history, findings of prior imaging studies, and any questions asked by the referring physician. The Procedures section (also known as "Techniques") describes the imaging protocols used in the current study. The Comparison section describes the prior study or studies the radiologist used as a benchmark or benchmarks for the current study. The Findings section describes the radiological findings of the current study. The Impression section summarizes the key findings, diagnosis, and recommendations.

The above description of a radiology study is intended to provide a general description of a typical layout and content of a radiology study. However, different systems or hospitals may have different layouts, headings, and content for radiology reports. The exemplary embodiments are not limited to any particular layout or content of a study. In fact, as will be described below, the exemplary embodiments allow the aggregation and summarization of varied radiology studies.

In complicated cases, such as for cancer patients, the patient may have many prior imaging studies for diagnosis, staging, treatment and follow-ups. Reports of such studies may become lengthy and, compounding the length and quantity of such reports, the information in the reports can be repeated. To keep up speed and work efficiently, a radiologist may only read the Impression section of the most recent report. By doing so, however, the radiologist can overlook relevant or even crucial information. Therefore, the exemplary embodiments may help a radiologist work efficiently while not missing important information.

Figure 1B:
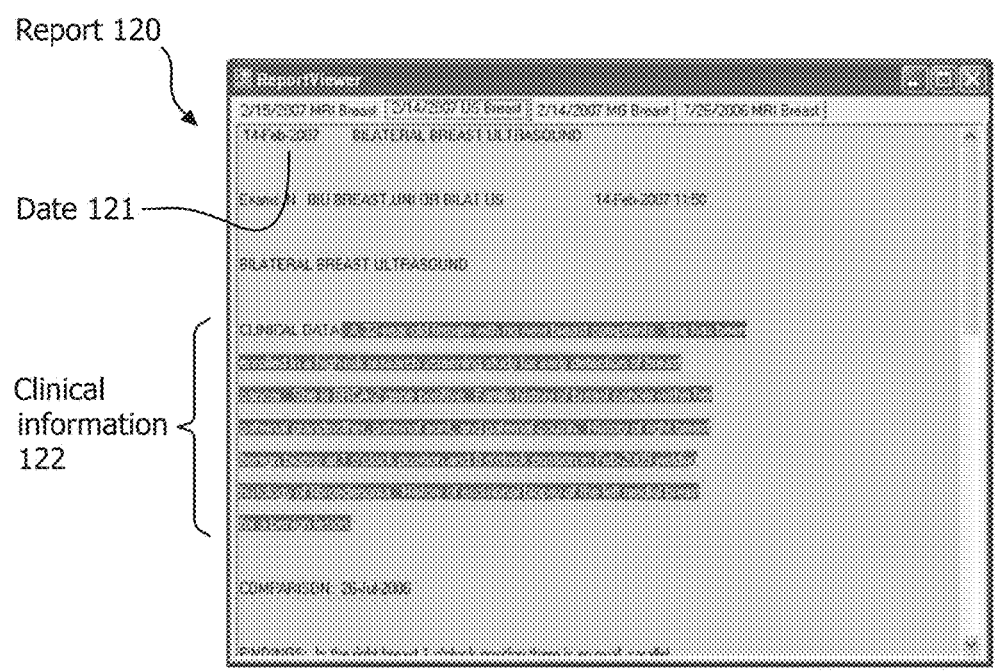
FIG. 1B shows an exemplary portion of a report of a second radiology study of the patient of FIG. 1A.

FIGS. 1A, 1B, 1C and 1D show four prior reports for the same patient; those of skill in the art will understand that the specific contents, formatting, and dates of the reports presented herein are only exemplary, and that the exemplary embodiments described hereinafter may be equally applicable to reports formatted in any other manner and containing any other set of data. FIG. 1A shows a first prior report 110. The report 110 includes date 111, indicating that the report is dated Feb. 15, 2007; typically, reports are provided in reverse chronological order starting with the most recent report, and the report 110 is the most recent of the four reports shown in FIGS. 1A-1D. The report 110 also includes Clinical Information section 112, shown in highlighted text. FIG. 1B shows a second prior report 120, including date 121 indicating that the report is dated Feb. 14, 2007, and Clinical Information section 122, shown in highlighted text.

Figure 1C:
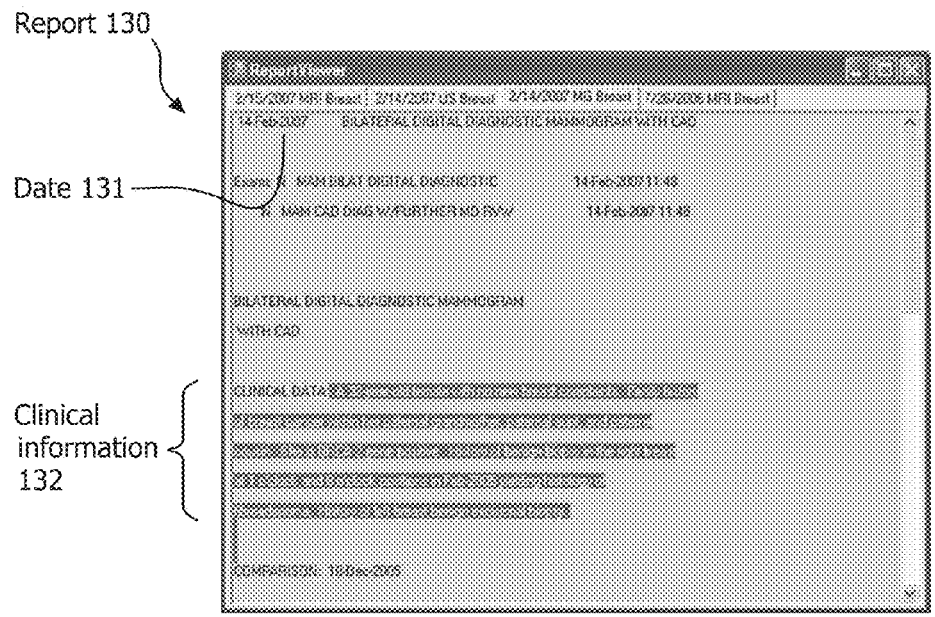
FIG. 1C shows an exemplary portion of a report of a third radiology study of the patient of FIG. 1A.
Figure 1D:
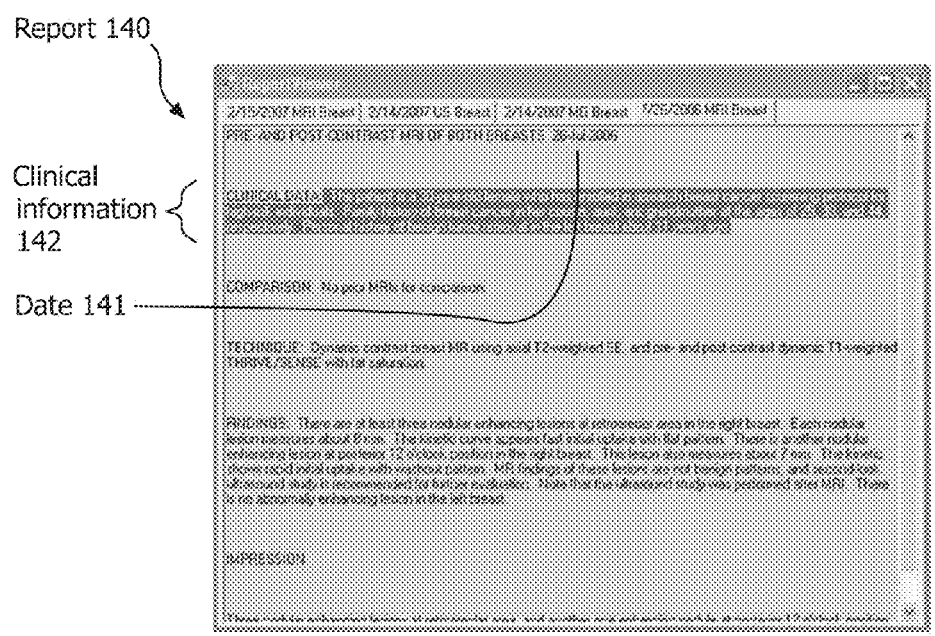
FIG. 1D shows an exemplary portion of a report of a fourth radiology study of the patient of FIG. 1A.

FIG. 1C shows a third prior report 130, including date 131 indicating that the report is dated Feb. 14, 2007, and Clinical Information section 132, shown in highlighted text. FIG. 1D shows a fourth prior report 140, including date 141 indicating that the report is dated Jul. 26, 2006, and Clinical Information section 142, shown in highlighted text. As FIGS. 1A-1D illustrate, the Clinical Information section of a report typically contains similar information as other reports of the same patient, though information reflected in the Clinical Information section can also change to reflect temporal changes of the patient. Optimally a radiologist would like to read all relevant clinical information from prior reports of the patient. The exemplary embodiments describe systems and methods for presenting a summarized view of clinical information in multiple reports, which may improve workflow efficiency for radiologists.

Figure 2:
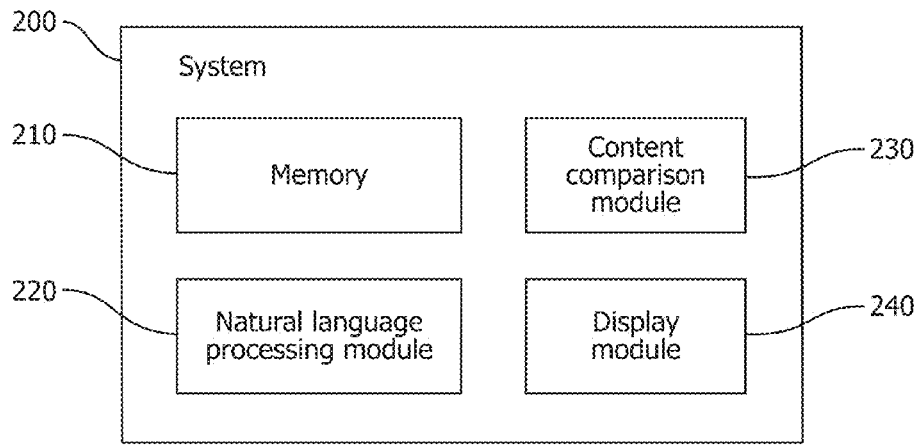
FIG. 2 shows an exemplary system for generating a summarized view of a plurality of reports of prior radiology studies.

FIG. 2 provides a schematic illustration for an exemplary system 200. Those of skill in the art will understand that, in one element, the "modules" illustrated may be modules of code stored in a non-transitory computer-readable memory and executed by a processor, to perform functions that will be described hereinafter. The system 200 includes a memory 210 storing archived reports for patients. The system 200 also includes a natural language processing module 220 operable to parse text documents (e.g., radiology, pathology, and laboratory reports) of a patient and extract lexicon and semantic information from each section of the documents.

The system 200 also includes a content comparison module 230 that compares the information from sentences in the Clinical Information section (or, alternately, the Impression section) of one report with the same section from other reports. The system 200 also includes a display module 240 providing for the presentation of information from the Clinical Information section (or, alternately, the Impression section) from multiple reports in a manner such that the information that is common to multiple reports is rendered differently from information that is distinct to one of the reports, as will be described in further detail below; in one embodiment, the display module 240 may be operable to present information from reports in a manner such that sentences that contain similar or redundant information are omitted.

Figure 3:
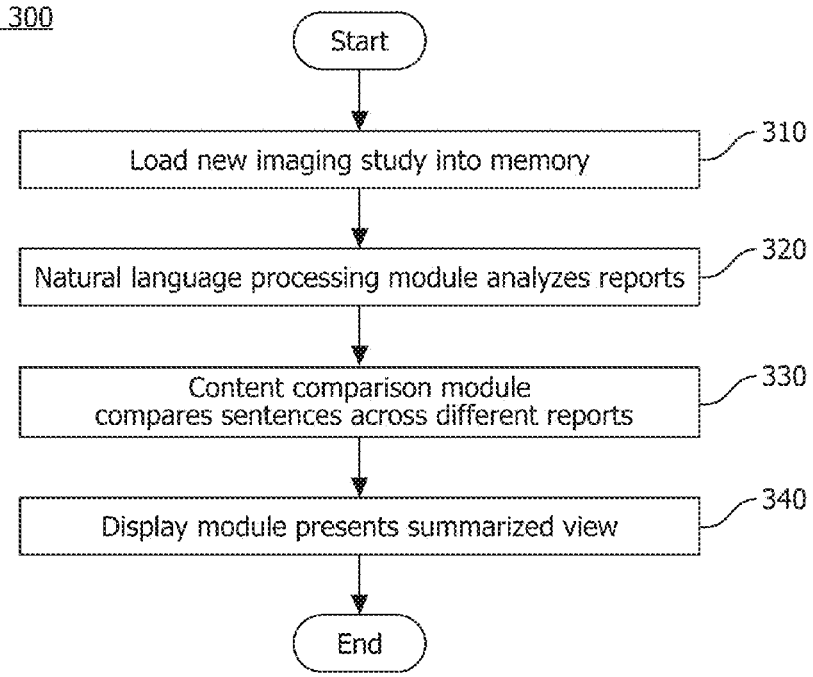
FIG. 3 shows an exemplary method for generating a summarized view of a plurality of reports of prior radiology studies.

FIG. 3 illustrates an exemplary method 300 by which text from multiple reports may be processed to provide a summarized view; the method 300 will be described with reference to the elements of the system 200, but those of skill in the art will understand that the method 300 may be implemented by any alternate system capable of doing so. In step 310, a new imaging study is loaded into the memory 210; this may be performed automatically at the conclusion of the study summarized by the report, manually at the prompting of a radiologist, periodically at set intervals for batch processing, or at any other point.

In step 320, the new imaging study and the "reason of exam" of the study, and prior reports for the same patient are analyzed by the natural language processing module 220; the prior reports may be retrieved from the memory 210 using any known manner of accomplishing this task, such as using the patient's name, birth date, social security number, patient identification number, or any other type of patient identifier. In this step, the natural language processing module 220 uses a statistical, rule-based, or other computational method (e.g., the methods used by software packages such as MedLEE, MetaMap, or OpenNLP) to determine sections, paragraphs, sentences, noun phrases, words of the reports, concepts, and (positive/negative) findings in the reports; those of skill in the art will understand that the software packages listed above are only exemplary, and that other techniques for extracting the same information are possible. Different sections within each report may be detected by identifying the headings of the sections, or other embedded information within each section; the natural language processing module 220 may be aware of synonyms for different types of sections in order to be able to determine that sections from two different reports with differing headings are functionally equivalent (e.g., may recognize that a section in one report titled "Clinical History" is the same as a section in another report titled "Clinical Information"). The natural language processing module 220 extracts the sentences from the Clinical Information section of each report (or, alternately, the Findings section and/or Impression section of each report).

In step 330, the content comparison module 230 compares sentences in a section from one report with the sentences from the same section from other reports. The comparison may be accomplished in a variety of manners, and those of skill in the art will understand that the processes described herein are only exemplary. Given any two sentences as input (e.g., a sentence in a section from one report, and a sentence from the corresponding section in another report), the content comparison module extracts words from both sentences and determines how many words are common to both sentences. In one embodiment, the content comparison module 230 considers the two sentences to be similar if the number of common words exceeds a threshold number. In another embodiment, the two sentences are considered to be similar if a relative value exceeds a threshold value; the relative value may be computed by dividing the number of common words by the total number of words of one of the two sentences, or the total number of combined words in the two sentences.

In some embodiments, the content comparison module 230 may disregard stop words (e.g., "is," "was," "has," etc.) in the determination of sentence similarity. In other embodiments, the content comparison module 230 may use, in the comparison, the linguistic stem or other tokens that can be derived from the words using rule-based and/or lexicon-based methods (e.g., the Porter stemming algorithm). In other embodiments, the content comparison module 230 may assign a statistic-based significance value to each word of the sentence, and, when determining the similarity of the two sentences, words may be weighted based on these significance values. The significance values may be derived from a set of training reports. In some embodiments, these training reports may be collected based on profiles. For example, a set of breast imaging reports may be collected to obtain the significance value per word, and the significance value assigned to a word may be its inverted document frequency ("IDF") value. Different sets of significance values may be determined for abdomen CT studies, neurological MRI studies, etc. In such an embodiment, the content comparison module 230 may first use the profile (e.g., body part, imaging modality, diagnosis) of the current report to retrieve the significance values of words before beginning the comparison of sentences.

In some embodiments, the natural language processing module 220 may determine the semantic category per word using ontologies such as Systematized Nomenclature of Medicine ("SNOMED") or Radiology Lexicon ("RADLEX"). In such embodiments, specific weights may be assigned to words from specific categories. For example, anatomy terms and diagnosis terms may be assigned higher weights than modifier words. Finally, in some embodiments, a combination of the above techniques may be used by the content comparison module 230 to compare sentences.

Alternately, the natural language processing module 220 can use natural language processing algorithms to extract noun phrases from the sentences, and then compare the noun phrases using the sentence comparison techniques described above. Additionally, to improve reliability, the natural language processing module 220 may apply a negation detection algorithm to determine the likelihood of a finding/diagnosis word (e.g., cancer, tumor, etc.) in a sentence, and use the likelihood information in the comparison. Additionally, the natural language processing module 220 can determine whether findings are acute and transient or chronic and persistent.

The above description of step 330 has related to the comparison of a single sentence from one report to a single sentence from another report. However, complete performance of step 330 entails the comparison of each sentence from each report to each sentence from each other report, and the end result of step 330 is a determination of whether each sentence from each report is similar to each sentence from each other report, using the similarity standards described above.

In step 340, the display module 240 presents, to a user of the system 200, a summarized view of the sentences in the Clinical Information sections of the reports. Initially, the display module 240 presents a full view of the sentences of the Clinical Information section of the most recent report of the patient. The sentences of the Clinical Information section may be presented line-by-line, for ease of reading and comparison. Alternatively, sentences may be presented as they are formatted in the original reports, and one sentence may occupy multiple lines. When there is insufficient room for display, sentences may be truncated.

Next, the display module 240 displays the sentences from the next most recent report in a manner that the sentences from the next most recent report that have been determined, in step 330, to be similar to a sentence in the most recent report are presented in a de-emphasized manner. In one embodiment, the similar sentences may be omitted; in another embodiment, they may be presented as " . . . ". In other embodiments, they may be de-emphasized in other manners, such as by display in fainter or smaller text, or in another manner not expressly described herein. Sentences from the next most recent report that have not been found to be similar to a sentence from the most recent report are displayed in the same manner as the sentences from the most recent report. In another embodiment, the display module 240 may also retain a full view of the first time that a given finding or diagnosis was made (e.g., the first diagnosis of cancer in the patient), even if the same finding has been restated in a more recent report. In another embodiment, the display module 240 may omit sentences containing past acute findings that do not impact disease management at the present; for example, if a report with the sentence "Fever, cold, vomiting" in the Clinical information section is five years old, this sentence may be omitted. The omitting of past acute findings may apply, for example, to acute findings that are older than a given threshold, such as four weeks.

The process described in the previous paragraph proceeds, in reverse chronological order, in a similar manner through all prior reports for the same patient, until the first (i.e., oldest) report is reached. For any given report, sentences may be de-emphasized, in the manner described above, if they are similar to any sentence of any of the preceding reports. Thus, the radiologist reviewing the reports provided by the display module 240 may be presented with a view that includes all significant information, excluding multiple versions of sentences that are common to multiple reports. After step 340, the method terminates.

Figure 4:
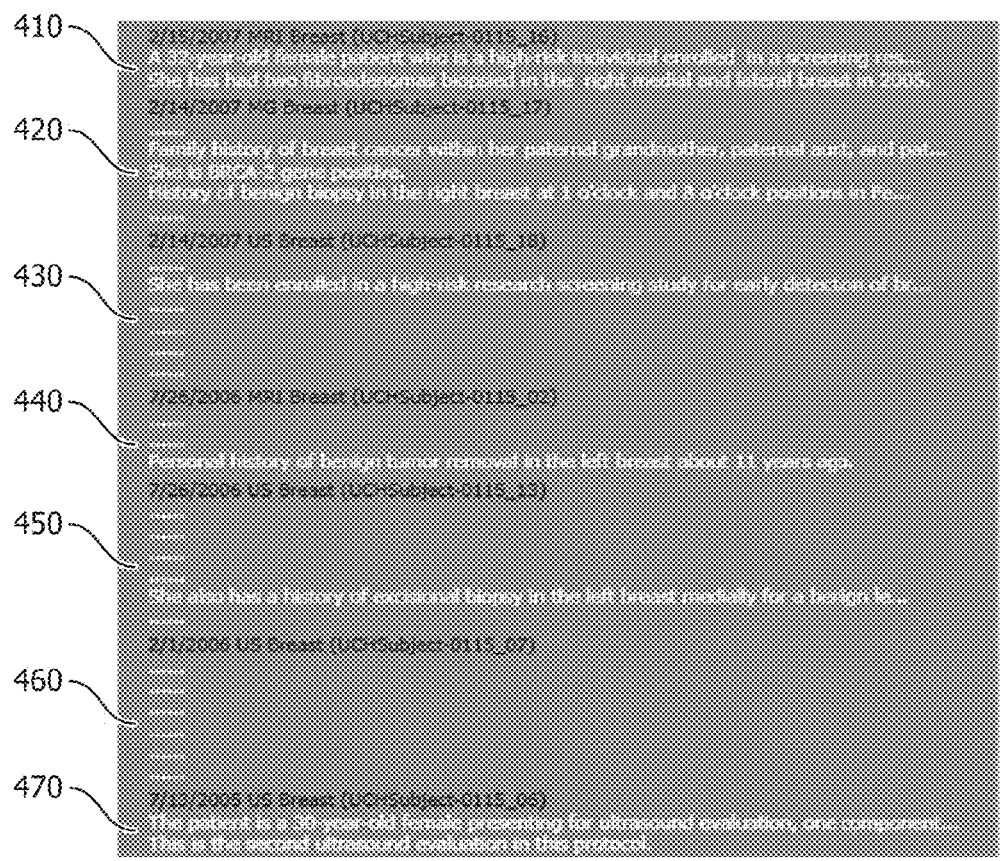
FIG. 4 shows an exemplary summarized view of a plurality of reports of prior radiology studies.

FIG. 4 illustrates a display 400 that may be provided by the display module 240 at the end of method 300. As described, the display 400 includes a full display of one of the sections (e.g., Clinical Information) of the most recent report 410. The display 400 also includes modified displays of the same section of previous reports 420, 430, 440, 450, 460 and 470 that replace sentences from the previous reports that have been determined to be similar (e.g., in step 330) to sentences that have already been displayed with " . . . " but include sentences that are dissimilar to the prior sentences from the already-shown reports.

Figure 5:
FIG. 5 shows a full non-summarized view of the plurality of reports of prior radiology studies of FIG. 4.

Alternately, FIG. 5 illustrates a display 500, which may be provided to a user who has made a request for more information from the display 400 of FIG. 4, including the full text of all reports 510, 520, 530, 540, 550, 560 and 570. It will be apparent to those of skill in the art that the display 400, produced by the system 200 and/or the method 300, provides a concise view that may enable optimization of the workflow of a radiologist reviewing the display 400, whereas the display 500 provides a more expanded view than the display 400 for a radiologist who desires more in-depth information about a patient while still being more concise and easier to read than the full text of the reports as illustrated above in FIGS. 1A-1D.

The user may have the option to make selections from the display 400 (e.g., by using a mouse or a touch-sensitive display to move a cursor and/or make a selection). In one embodiment, if the user hovers a cursor over one of the reports that has had one or more of its sentences displayed as described above, the display 400 may provide the user with the full text of that report. In another embodiment, the user may have the option to request the full text of all of the reports; in such an embodiment, the display 400 would update to show the user the full display 500, as described above. In another embodiment, the user may have the option to enter a search term and view filtered information based on the search term. For example, if the user enters a search term "recommendation," the content comparison module 230 may extract all sentences containing "recommendation," and apply the techniques described above only to those sentences, to provide a summarized view of only those sentences.

The exemplary system 200 and method 300 have been described with specific reference to the Clinical Information section of a report. However, as described above, the system may alternately be used to summarize other sections of reports, such as the Impression section. The exemplary system 200 and method 300 may thus provide a user (e.g., a radiologist) with displays 400 and 500 that present a concise, summarized view of text from reports of a patient's prior radiology studies, in order to enable the radiologist to obtain the proper context for a current study in a more time-efficient and effective manner.

Figure 6:
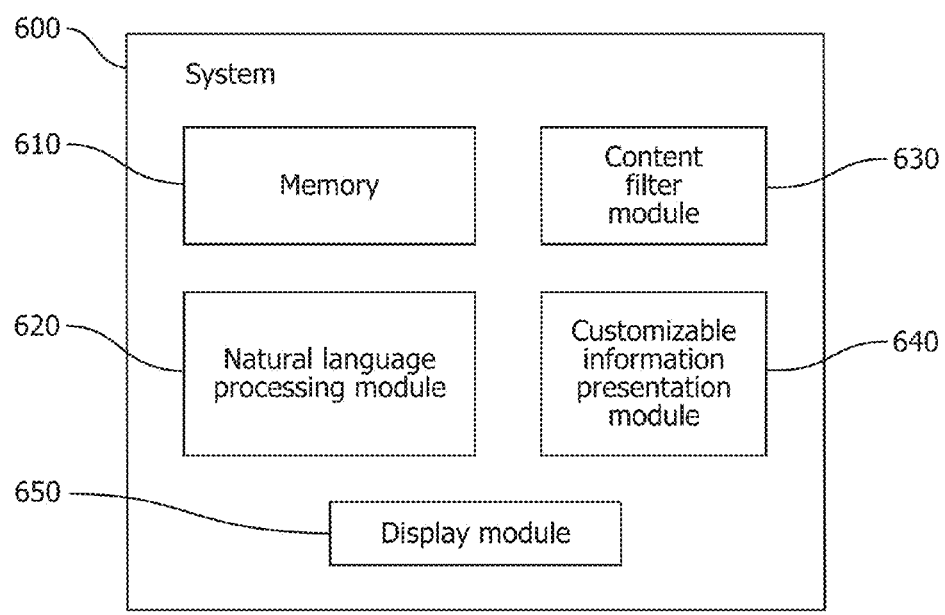
FIG. 6 shows an exemplary system for generating a dashboard view of a plurality of reports of prior radiology studies.

FIG. 6 illustrates a second exemplary system 600 for providing a different type of summary view to a user. The system 600 includes a memory 610 and a natural language processing module 620, which are substantially similar to the memory 210 and natural language processing module 220 described above with reference to the system 200. The system 600 also includes a content filter module 630 that determines relevant pieces of information based on ontologies and/or statistical natural language processing methods.

The system 600 also includes a customizable information presentation module 640 that may present the filtered information generated by content filter module 630 depending on the properties of the current study to be performed by the radiologist. In one embodiment, the customizable information presentation module 640 may present the information on a time line. The customizable information presentation module 640 may be able to detect, based on the filtered information, episodes of conditions such as breast cancer, broken bones, etc. The system 600 also includes a display module 650 that provides a dashboard-like GUI presenting the filtered information. As described above with reference to system 200, the modules of the system 600 may be software modules embodied in a non-transitory computer-readable storage medium and executable by a processor.

Figure 7:
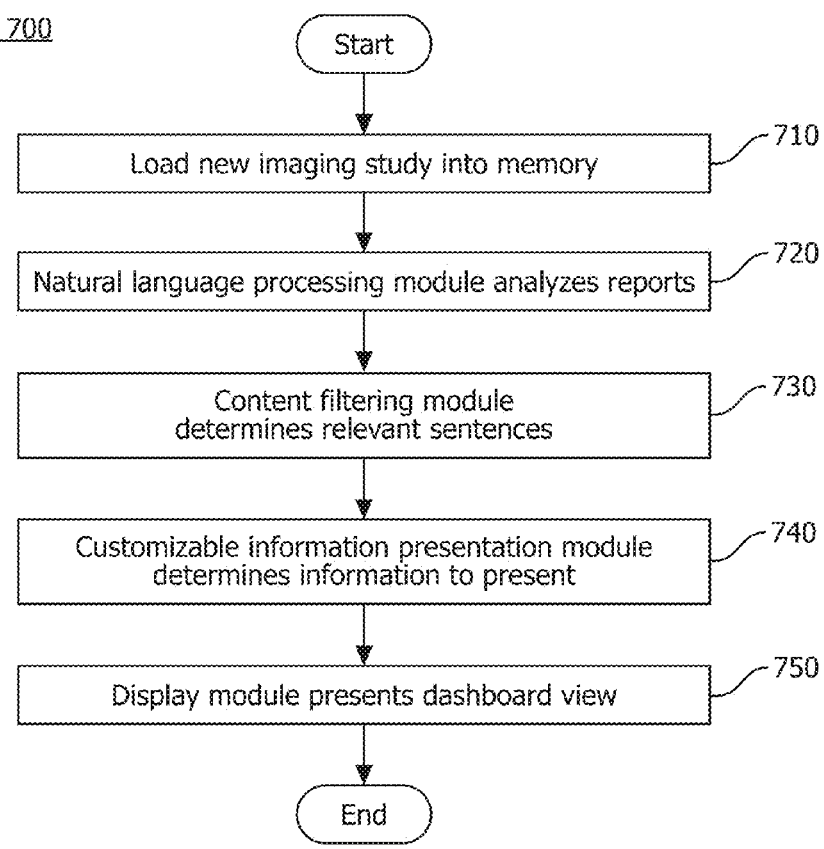
FIG. 7 shows an exemplary method for generating a dashboard view of a plurality of reports of prior radiology studies.

FIG. 7 illustrates an exemplary method 700 by which text from multiple reports may be processed to provide a dashboard view; the method 700 will be described with reference to the elements of the system 600, but those of skill in the art will understand that the method 700 may be implemented by any alternate system capable of doing so. In step 710, a new imaging study is loaded into the memory 610; as described above with reference to step 310 of method 300, this may be performed automatically at the conclusion of the study summarized by the report, manually at the prompting of a radiologist, periodically at set intervals for batch processing, or at any other point.

In step 720, the natural language processing module 620 analyzes the text reports of all prior studies of the patient. As described above with reference to step 320 of method 300, prior reports may be retrieved from the memory 210 using any known manner of accomplishing this task, and the natural language processing module 720 may analyze the text using a proprietary or third-party software package such as MedLEE, MetaMap, or OpenNLP to determine sections, paragraphs, sentences, noun phrases, and words of the reports; those of skill in the art will understand that the software packages listed above are only exemplary, and that other techniques for extracting the same information are possible. Additionally, the natural language processing module 620 may analyze the sentences contained therein, and medical concepts may be extracted using an engine such as SNOMED or RADLEX. Furthermore, the natural language processing module 620 may determine the likelihood of findings (e.g., positive, most likely, likely, less likely, negative) based on the text content of the reports.

In step 730, the content filtering module 630 determines which sentences or phrases of prior reports contain potentially relevant information. This determination may be made in a variety of manners. In a first exemplary embodiment, the content filtering module 630 may include a predefined set of keywords (e.g., "carcinoma," "DCIS," "suspicious," "follow-up," "suspicions," "liver cancer," etc.). If the content filtering module 630 detects any of the keywords in a sentence, the sentence is determined to be relevant.

In a second exemplary embodiment, the content filtering module 630 may be provided with a predefined set of keywords as described above, but is further operable to expand the set of keywords, using an ontology such as SNOMED or RADLEX. For each of the predefined terms, the system finds corresponding concepts, such as through the use of SNOMED, and extracts acronyms and synonyms of the concepts. For example, if one of the keywords is "DCIS," the content filtering module consults a resource such as SNOMED to determined that "DCIS" is an acronym for "ductal carcinoma in situ," and then further finds synonyms "tumor" and "cancer" for "carcinoma." A sentence is then considered to be relevant if the content filtering module 630 determines that it contains any of the keywords or any of what it has determined to be related concepts.

In a third exemplary embodiment, the content filtering module 630 may use statistical natural language processing methods to determine which sentences are relevant. For example, the content filtering module 630 may receive a set of documents that has been annotated by a group of radiologists to indicate which sentences from which sections are relevant for subsequent presentation. The content filtering module 630 may then use the received documents and their annotations to train machine learning algorithms using features as described above, and may then mimic how a radiologist would determine the relevance of sentences in the reports. The annotation and training process may be done in advance as a pre-provisioning process, or during the performance of the method 700.

Once the content filtering module 630 has determined, in step 730, which sentences from prior reports are relevant, in step 740, the customizable information presentation module 640 determines what information should be presented. In order to accomplish this, the customizable information presentation module 640 may extract, from the Clinical Information sections of prior reports, sentences mentioning family history, risk factors, and diagnosis. These sentences may then be sorted by time and presented in a list; the most recent sentence may be presented as a "History" entry in an initial dashboard view, as will be described below.

The customizable information presentation module 640 may further extract, from the Impression sections of prior reports, sentences that mention recommendations of follow-up procedures. As above, these sentences may be sorted by time, and the most recent sentence may be presented as a "Recommendations" entry in an initial dashboard view, as will be described in further detail below. The customizable information presentation module 640 may further extract, from the Findings section of prior reports, sentences containing a reference to follow-up recommendations. These sentences may then be sorted by time, and the most recent such sentence may be presented in an "Incidental Followups" entry in an initial dashboard view, as will be described in further detail below. Those of skill in the art will understand, however, that the information to be extracted by the customizable information presentation module 640 may vary among differing embodiments, and may be customized by the radiologist, and that the specific information described above is only exemplary.

Figure 8:
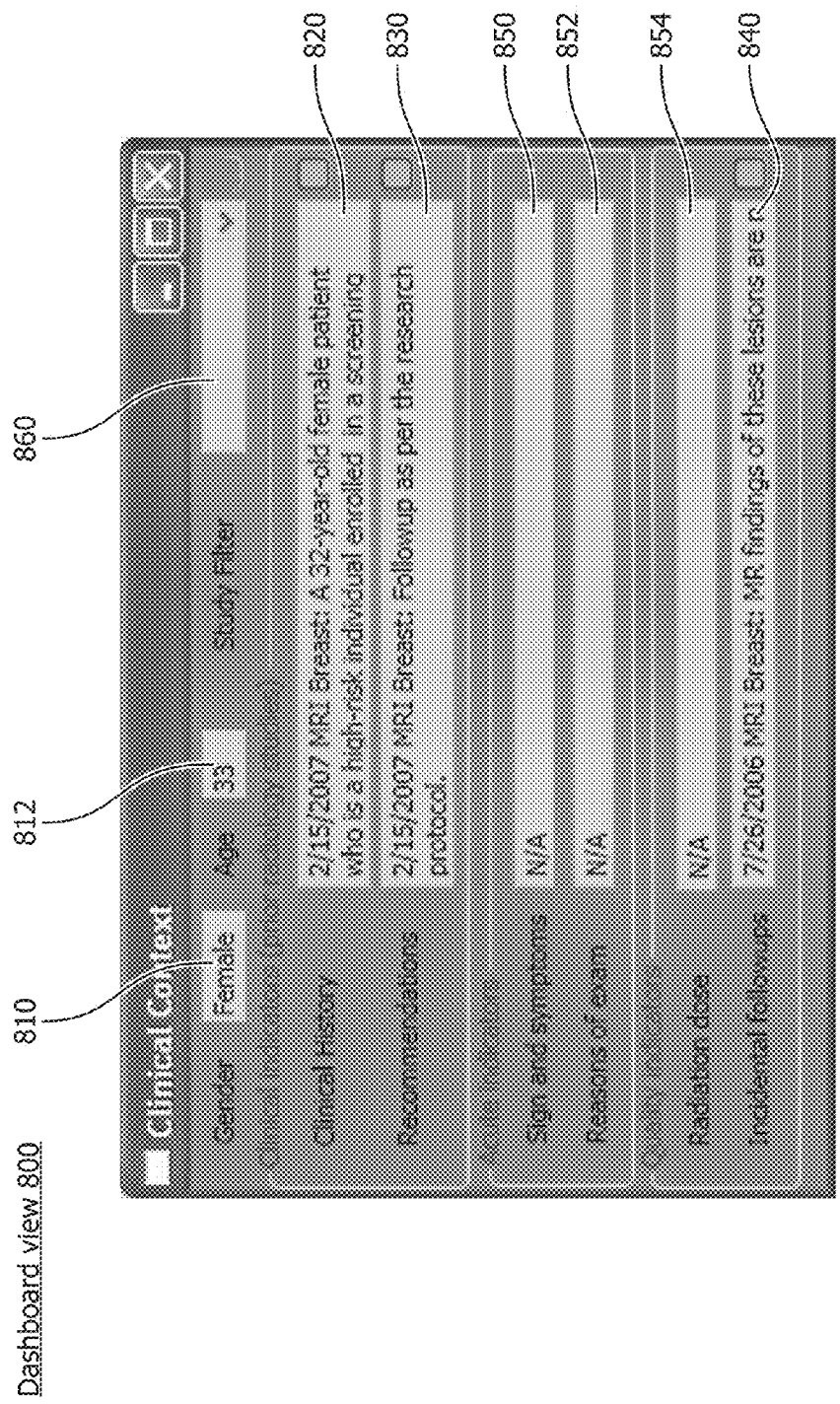
FIG. 8 shows an exemplary dashboard view of a plurality of reports of prior radiology studies.

In step 750, the display module 650 presents a dashboard view of the information extracted by the customizable information presentation module 640 in step 740. Following step 750, the method 700 terminates. FIG. 8 illustrates an exemplary dashboard view 800 that may be generated by the display module 650 in step 750. The dashboard view 800 may include basic patient information, such as the patient's gender 810 and age 812. Additionally, the dashboard view 800 may display extracted information, as described above. The dashboard view 800 may include a Clinical History field 820, a Recommendations field 830, and an Incidental Followups field 840, all of which were described above with reference to the customizable information presentation module 640.

The dashboard view 800 may also include additional fields 850, 852 and 854, which may vary among differing embodiments, and may be extracted from other portions of the reports described above, or, alternately, from other sources such as pathology reports, lab reports, etc. In the illustrated embodiment, dashboard view 800 includes Sign and Symptoms field 850, Reasons of Exam field 852, and Radiation Dose field 854. In one exemplary embodiment, information from a computerized physician order entry ("CPOE") system, including the patients signs and symptoms and the reason of exam made by the referring physician, may be parsed for display in an Acute Indicators section of the dashboard 800. The dashboard view 800 may also include a study filter 860, which may be implemented using a drop-down interface or any other mechanism for allowing a user to select from a variety of options. Using the study filter 860, the user may select only one type of study (e.g., MRI, ultrasound, etc.), and have the information displayed in the dashboard view 800 limited to information extracted from reports of the selected type of study. This may be accomplished using standard filtering techniques.

In one exemplary embodiment, when the user selects one section of the dashboard view 800 (e.g., by hovering a mouse cursor over the selected section or selecting the section with a touch-sensitive display), the dashboard view 800 may display a pop-up window including the full list of information for the selected section, sorted in reverse chronological order, rather than simply the most recent sentence shown in the dashboard view. For example, if the user selects the Clinical History field 820, the dashboard view 800 may update to show the user the full set of entries from the Clinical Information sections of all the prior reports; this may be a display similar to the display 500 illustrated in FIG. 5 and displayed above. In another exemplary embodiment, the dashboard 800 may simply present the most recent information for the patient; the specific type of view to be presented in the dashboard may also be customized by the user (e.g., the radiologist).

Figure 9A:
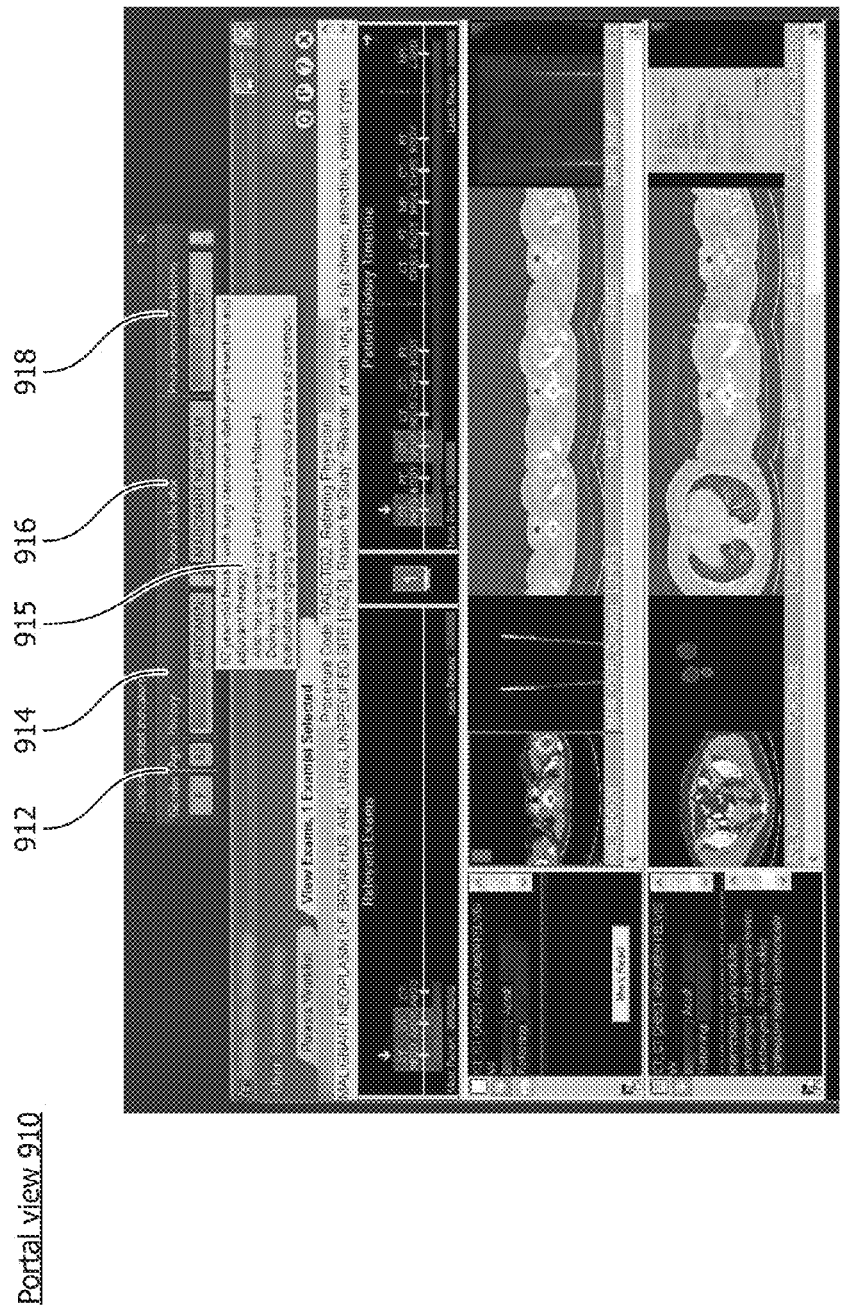
FIG. 9A shows a first exemplary view of a radiology portal providing information from prior radiology studies.

In one exemplary embodiment, the views described above may be accessed from a general-purpose radiology portal, and information may be accessed by making selections from appropriate sections of the display of such a portal. FIG. 9A illustrates a first exemplary portal view 910. The lower portion of the display presents standard options for viewing radiology test results, and will not be described in detail herein. The portal view 910 includes patient information 912, a history section 914, an acute indicator section 916, and a prior recommendations section 918. If the user makes an initial selection of the history section 914 (e.g., by hovering with a mouse cursor or making a single tap on a touch-sensitive display), a pop-up history display 915 may be shown within portal view 910. The pop-up history display 915 may show a summarized view of patient history information extracted from the Clinical Information sections of reports as described above. In one exemplary embodiment, this may be the entire Clinical information section of the most recent report.

Figure 9B:
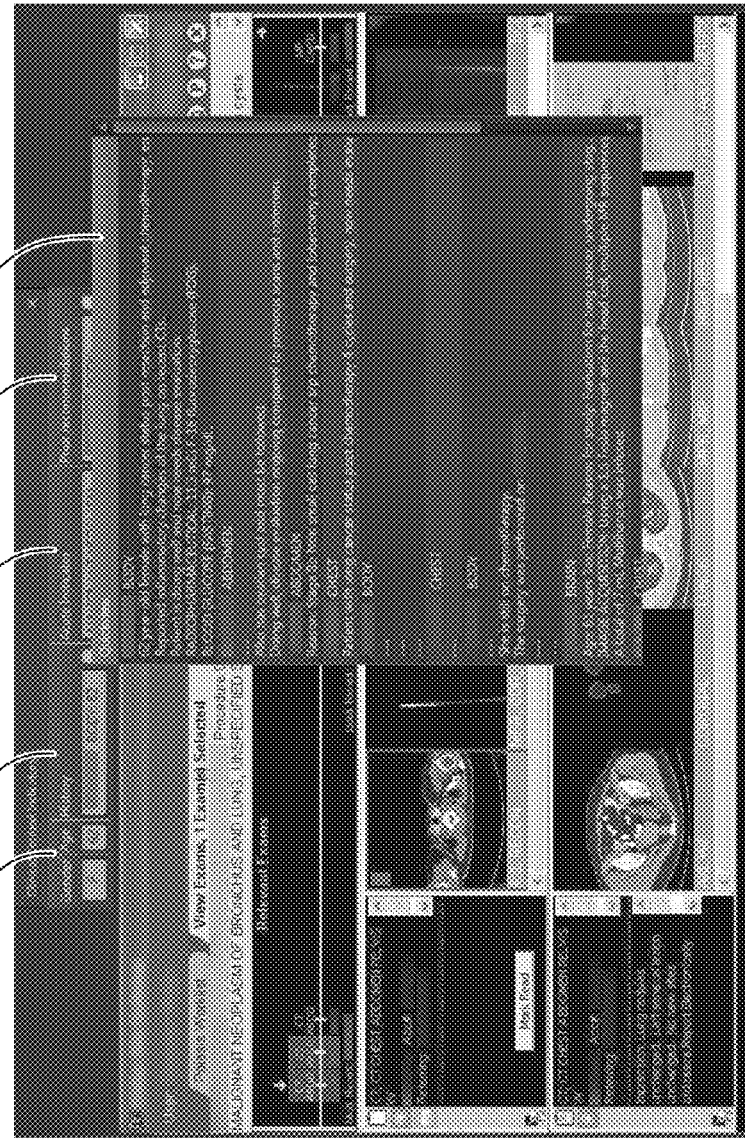
FIG. 9B shows a second exemplary view of a radiology portal providing information from prior radiology studies.

FIG. 9B illustrates a second exemplary portal view 920. Like the first exemplary portal view 910, the second exemplary portal view 910 includes patient information 922, a history section 924, an acute indicator section 926, and a prior recommendations section 928. If the user makes a follow-up selection of the history section 924 (e.g., by clicking with a mouse or touchpad, or making a double tap on a touch-sensitive display), an expanded pop-up history display 925 may be shown within portal view 920. The expanded pop-up history display 925 may show an expanded view of patient history information extracted from the Clinical Information sections of reports as described above. In one exemplary embodiment, this may be the display 400 described above with reference to FIG. 4.

Figure 9C:
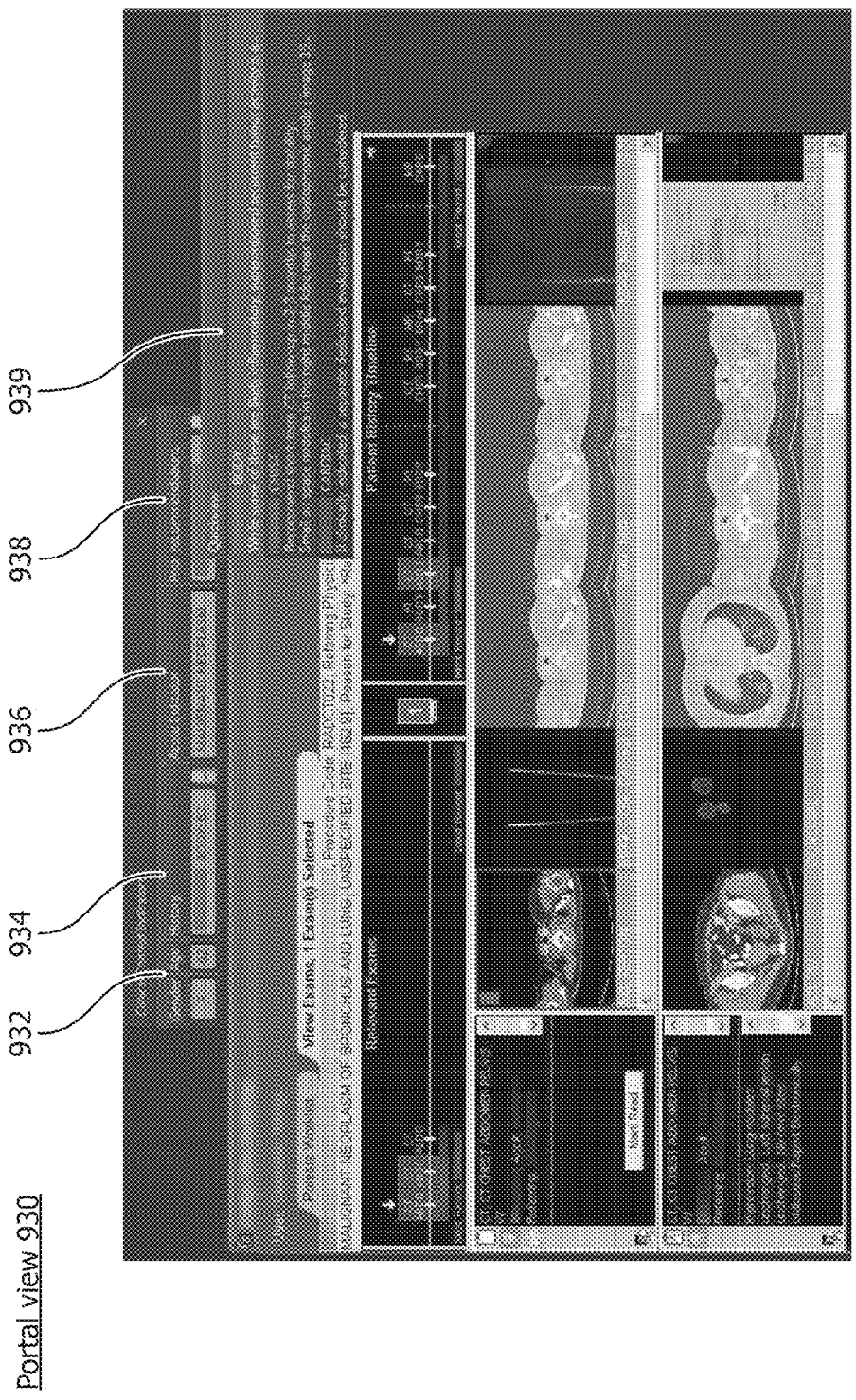
FIG. 9C shows a third exemplary view of a radiology portal providing information from prior radiology studies.

FIG. 9C illustrates a third exemplary portal view 930. Like the previously-described exemplary portal views, the third exemplary portal view 930 includes patient information 932, a history section 934, an acute indicator section 936, and a prior recommendations section 938. If the user makes a selection of the prior recommendations section 938 (e.g., by hovering with a mouse cursor or making a single tap on a touch-sensitive display), a pop-up prior recommendations display 939 may be shown within portal view 930. The pop-up prior recommendations display 939 may show a summarized view of prior recommendations extracted from the Impression sections of reports as described above. In one exemplary embodiment, this may be similar to the Recommendations field 830 of the dashboard view 800. In the exemplary portal view 930, the prior recommendations display 939 includes separate recommendations for separate body parts of the patient; these may be separated by extracting the appropriate body parts (e.g., body, chest, cardiac) from sentences of the Impression fields of prior reports, and including the most recent relevant sentence for each body part.

It will be apparent to those of skill in the art that the information presented in portal views 910, 920 and 930 is similar to that presented in dashboard view 800, and that portal views 910, 920 and 930 therefore present an alternative embodiment of the dashboard view 800. For example, history section 914 presents information similar to that in Clinical History field 820, prior recommendations section 918 presents information similar to that in Recommendations field 830 and Incidental Followups field 840, and acute indicator section presents information similar to that in Sign and Symptoms field 850 and Reasons of Exam field 852. Similarly, it will be apparent to those of skill in the art that the information described above, or similar information, may be presented in graphical displays that differ from those described herein, without departing from the broader scope of the exemplary embodiments.

The exemplary embodiments described above provide radiologists with various streamlined and concise ways in which to view reports of prior studies. These views may include a summarized text version of the same section from a set of previous reports, a dashboard view providing most recent information of various types, and information embedded within a general radiology portal. By providing data in these manners, it may be easier for radiologists to review all relevant information, without reading repeated copies of the same information, in order to obtain the proper context for a current study with greater efficiency, and optimize the radiologist's overall workflow as a result.

As noted above, it will be apparent to those of skill in the art that, though the exemplary embodiments described above make specific reference to radiologists and radiology studies, the broader principles outlined herein may also be equally applicable to the aggregation of any other type of patient medical data for presentation to any other type of medical professional. Those of skill in the art will understand that various embodiments may differ from the exemplary embodiments described above, without departing from the broader scope of this disclosure. Those of skill in the art will understand that the above-described exemplary embodiments may be implemented in any number of matters, including as a software module, as a combination of hardware and software, etc. For example, the methods 300 and 700 may be embodied in a program stored in a non-transitory storage medium and containing lines of code that, when compiled, may be executed by a processor.

It is noted that the claims may include reference signs/numerals in accordance with PCT Rule 6.2(b). However, the present claims should not be considered to be limited to the exemplary embodiments corresponding to the reference signs/numerals.

It will be apparent to those skilled in the art that various modifications may be made to the exemplary embodiments, without departing from the spirit or the scope of the invention. Thus, it is intended that the present invention cover modifications and variations of this invention provided they come within the scope of the appended claims and their equivalents.

What is claimed is:

1. A method, comprising:
receiving a plurality of medical reports, each medical report including a plurality of sections, each of the sections including text content;
correlating corresponding sections of each of the medical reports into section types;
extracting the text content of the sections of the medical reports for a selected section type;
aggregating, into a single display, the text content of the sections of all the medical reports for the selected section type;
determining a reduced set of text content to be displayed in the single display,
wherein the determining the reduced set of text content comprises filtering the text content based on a set of keywords and phrases relevant to a current medical study and determining common text content from earlier medical reports using natural language processing;
wherein the set of keywords and phrases relevant to the current medical study is generated using an ontology to find secondary keywords and phrases related to each of a predefined set of keywords and phrases;
wherein, for each of the predefined keywords and phrases, the ontology finds corresponding concepts and extracts acronyms and synonyms of the concepts to add to the set of keywords and phrases; and
displaying, in the single display, the reduced set of text content of the sections of all the medical reports for the selected section type,
wherein the common text content from earlier medical reports is represented in the single display in a de-emphasized manner.

2. The method of claim 1, further comprising:
removing, from the single display, text content that includes information that is duplicative of information that is included in other text content.

3. The method of claim 2, wherein the medical reports have a chronological order and the removing is based on removing text content including information of earlier medical reports that is duplicative of information in later medical reports.

4. The method of claim 2, wherein the medical reports have a chronological order and the removing is based on removing text content including information of earlier medical reports that is one of acute and transient.

5. The method of claim 1, wherein the medical reports are imaging studies.

6. The method of claim 1, wherein the correlating corresponding sections includes:
identifying corresponding sections based on information in each medical report designating sections, wherein the information includes one of a heading of each section or embedded information within each of the sections.

7. The method of claim 1, wherein the medical reports have a chronological order.

8. A method, comprising:
receiving a plurality of medical reports, each medical report including a plurality of sections, each of the sections including text content;
correlating corresponding sections of each of the medical reports into section types;
extracting the text content of the sections;
determining a reduced set of text content to be displayed for each of the section types,
wherein the determining the reduced set of text content comprises filtering the text content based on a set of keywords and phrases relevant to a current medical study and determining common text content from earlier medical reports using natural language processing;
wherein the set of keywords and phrases relevant to the current medical study is generated using an ontology to find secondary keywords and phrases related to each of a predefined set of keywords and phrases;
wherein, for each of the predefined keywords and phrases, the ontology finds corresponding concepts and extracts acronyms and synonyms of the concepts to add to the set of keywords and phrases; and
displaying, in a single display, the reduced set of text content of the sections of all the medical reports for the selected section type,
wherein the common text content from earlier medical reports is represented in the single display in a de-emphasized manner.

9. The method of claim 8, wherein the displaying is based on a chronological order of the medical reports.

10. The method of claim 8, wherein the determining the reduced set of text content is based on analyzing the text content and selecting the reduced set of text content based on predefined criteria.

11. The method of claim 8, wherein the reduced set of text content is based on a determination of relevant sentences or phrases in each of the sections.

12. The method of claim 11, wherein relevant sentences or phrases are determined based on the presence or absence of keywords in the sentences or phrases.

13. The method of claim 12, wherein the keywords are definable by a user.

14. The method of claim 8, wherein the display of the reduced set of text content is sortable by a user.

15. A system, comprising:
a memory storing a plurality of medical reports, each medical report including a plurality of sections, each of the sections including text content; and
a processor executing a set of instructions to perform a method, comprising,
correlating corresponding sections of each of the medical reports into section types;
extracting the text content of the sections of the medical reports for a selected section type;
aggregating, into a single display, the text content of the sections of all the medical reports for the selected section type;
determining a reduced set of text content to be displayed in the single display,
wherein the determining the reduced set of text content comprises filtering the text content based on a set of keywords and phrases relevant to a current medical study and determining common text content from earlier medical reports using natural language processing;
wherein the set of keywords and phrases relevant to the current medical study is generated using an ontology to find secondary keywords and phrases related to each of a predefined set of keywords and phrases;
wherein, for each of the predefined keywords and phrases, the ontology finds corresponding concepts and extracts acronyms and synonyms of the concepts to add to the set of keywords and phrases; and displaying, in the single display, the reduced set of text content of the sections of all the medical reports for the selected section type,
wherein the common text content from earlier medical reports is represented in the single display in a de-emphasized manner.

16. The system of claim 15, wherein the method further comprises:
    determining a reduced set of text content to be displayed for each of the section types.

17. The system of claim 15, wherein the medical reports have a chronological order and the de-emphasizing is based on removing text content including information of earlier medical reports that is duplicative of information in later medical reports.

* * * * *